(12) United States Patent
Blake

(10) Patent No.: US 10,117,717 B2
(45) Date of Patent: Nov. 6, 2018

(54) CATHETER DRESSING SYSTEM

(71) Applicant: Luke Blake, Terre Haute, IN (US)

(72) Inventor: Luke Blake, Terre Haute, IN (US)

( * ) Notice: Subject to any disclaimer, the term of this patent is extended or adjusted under 35 U.S.C. 154(b) by 3 days.

(21) Appl. No.: 15/377,146

(22) Filed: Dec. 13, 2016

(65) Prior Publication Data

US 2018/0161116 A1    Jun. 14, 2018

(51) Int. Cl.
*A61B 46/20*      (2016.01)
*A61B 46/23*      (2016.01)
*A61M 25/02*     (2006.01)

(52) U.S. Cl.
CPC ............. *A61B 46/23* (2016.02); *A61M 25/02* (2013.01); *A61B 2046/205* (2016.02); *A61B 2046/234* (2016.02)

(58) Field of Classification Search
CPC .............. A61B 46/00; A61B 2046/205; A61B 2046/234; A61B 2050/002; A61B 46/20
USPC .................................................... 604/385.05
See application file for complete search history.

(56) References Cited

U.S. PATENT DOCUMENTS

| | | | |
|---|---|---|---|
| 3,916,887 A | * | 11/1975 | Kelly ...................... A61B 46/00 128/851 |
| 4,324,237 A | | 4/1982 | Buttaravoli |
| 4,743,232 A | * | 5/1988 | Kruger .................. A61F 13/023 128/DIG. 26 |
| 4,875,473 A | | 10/1989 | Alvarez |
| 5,344,415 A | | 9/1994 | deBusk et al. |
| 5,707,348 A | | 1/1998 | Krogh |
| 6,090,076 A | | 7/2000 | Lane, Jr. |
| 6,124,521 A | | 9/2000 | Roberts |
| 6,132,399 A | | 10/2000 | Shultz |
| 6,988,511 B2 | | 1/2006 | Tang |
| 8,029,479 B2 | | 10/2011 | Guthrie |

* cited by examiner

*Primary Examiner* — Deanna K Hall

(57) ABSTRACT

A catheter dressing system includes a catheter that may be inserted into a patient when the patient is undergoing a surgical procedure. A dressing is provided and the dressing is selectively adhered to the patient. The dressing covers the catheter thereby inhibiting the catheter from being contaminated and the dressing gas a tear-away portion. A surgical drape is positioned on the patient when the patient is undergoing the surgical procedure. The surgical drape adhesively engages the tear-away portion of the dressing. The tear away portion is removed from the dressing when the surgical drape is removed from the patient such that the dressing remains on the catheter.

8 Claims, 4 Drawing Sheets

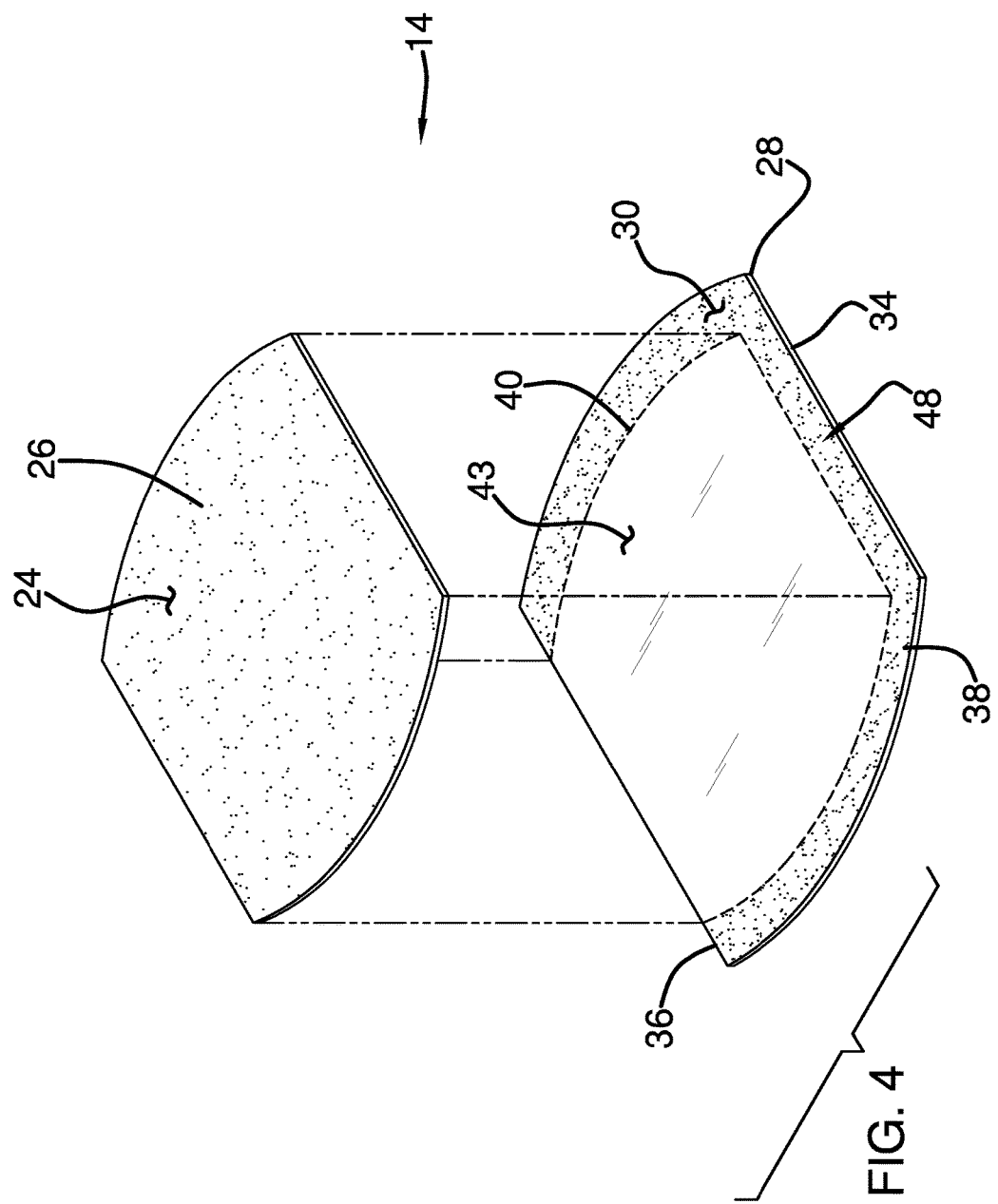

CATHETER DRESSING SYSTEM

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIE THE OFFICE ELECTRONIC FILING SYSTEM.

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to dressing devices and more particularly pertains to a new dressing device for facilitating a dressing to be retained on a catheter when a surgical drape is removed from a patient.

BRIEF SUMMARY OF THE INVENTION

An embodiment of the disclosure meets the needs presented above by generally comprising a catheter that may be inserted into a patient when the patient is undergoing a surgical procedure. A dressing is provided and the dressing is selectively adhered to the patient. The dressing covers the catheter thereby inhibiting the catheter from being contaminated and the dressing has a tear-away portion. A surgical drape is positioned on the patient when the patient is undergoing the surgical procedure. The surgical drape adhesively engages the tear-away portion of the dressing. The tear away portion is removed from the dressing when the surgical drape is removed from the patient such that the dressing remains on the catheter.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 4 is an exploded view of dressing of an embodiment of the disclosure.

DETAILED DESCRIPTION OF THE INVENTION

Figure 1:
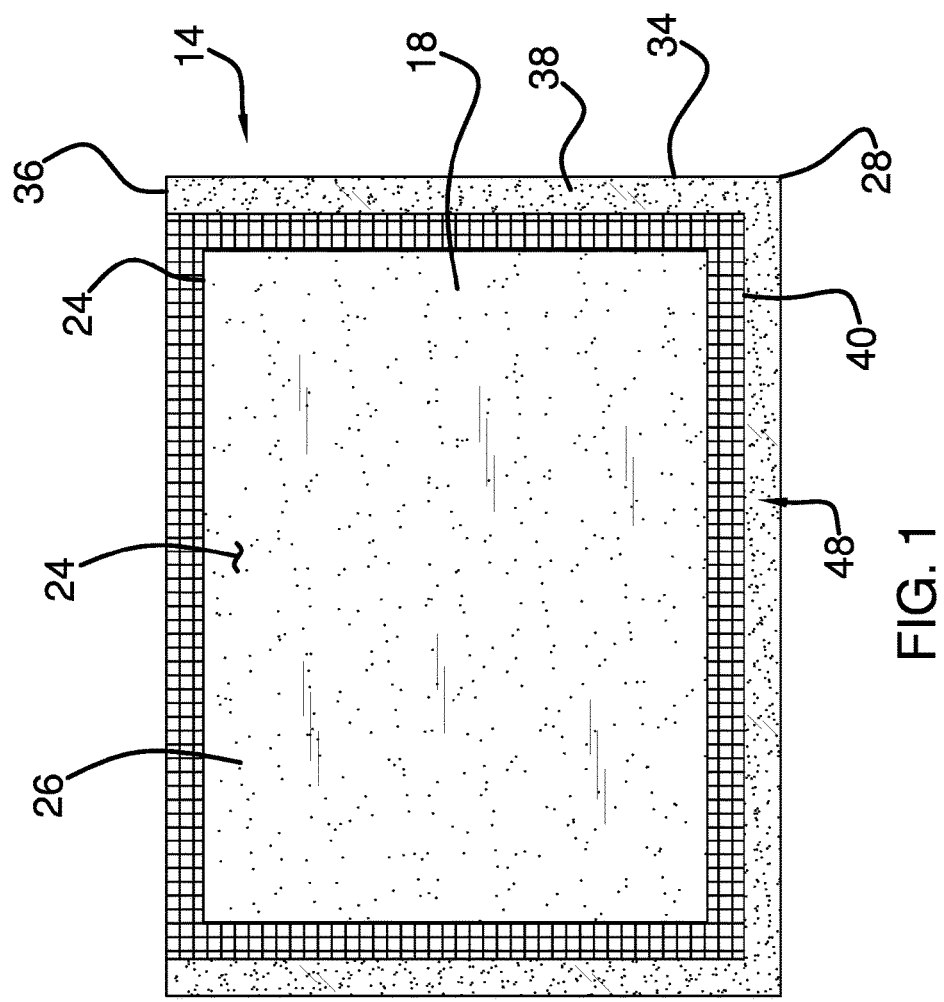
FIG. 1 is a bottom view of a dressing of a catheter dressing system according to an embodiment of the disclosure.
Figure 2:
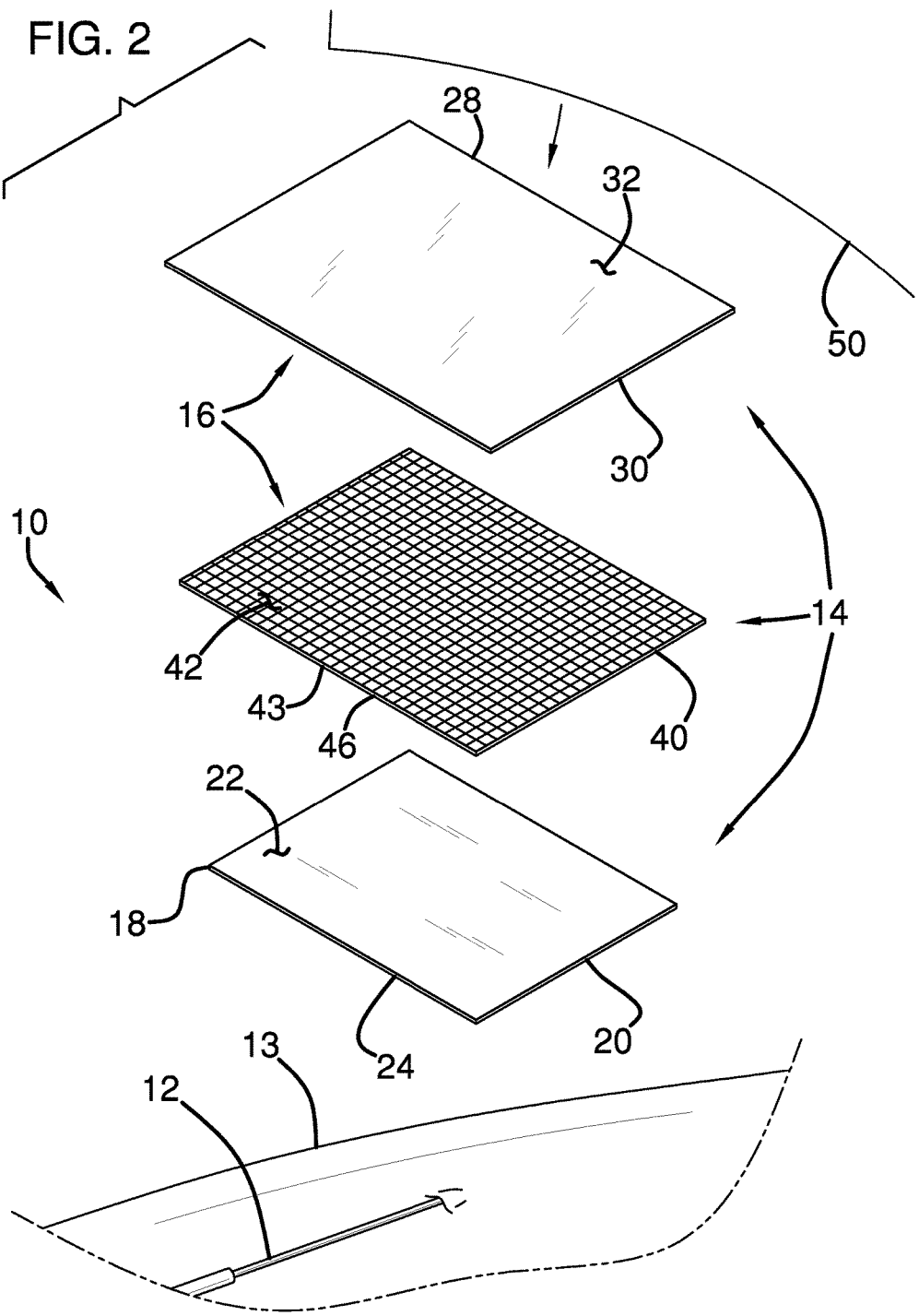
FIG. 2 is an exploded perspective view of an embodiment of the disclosure.
Figure 3:
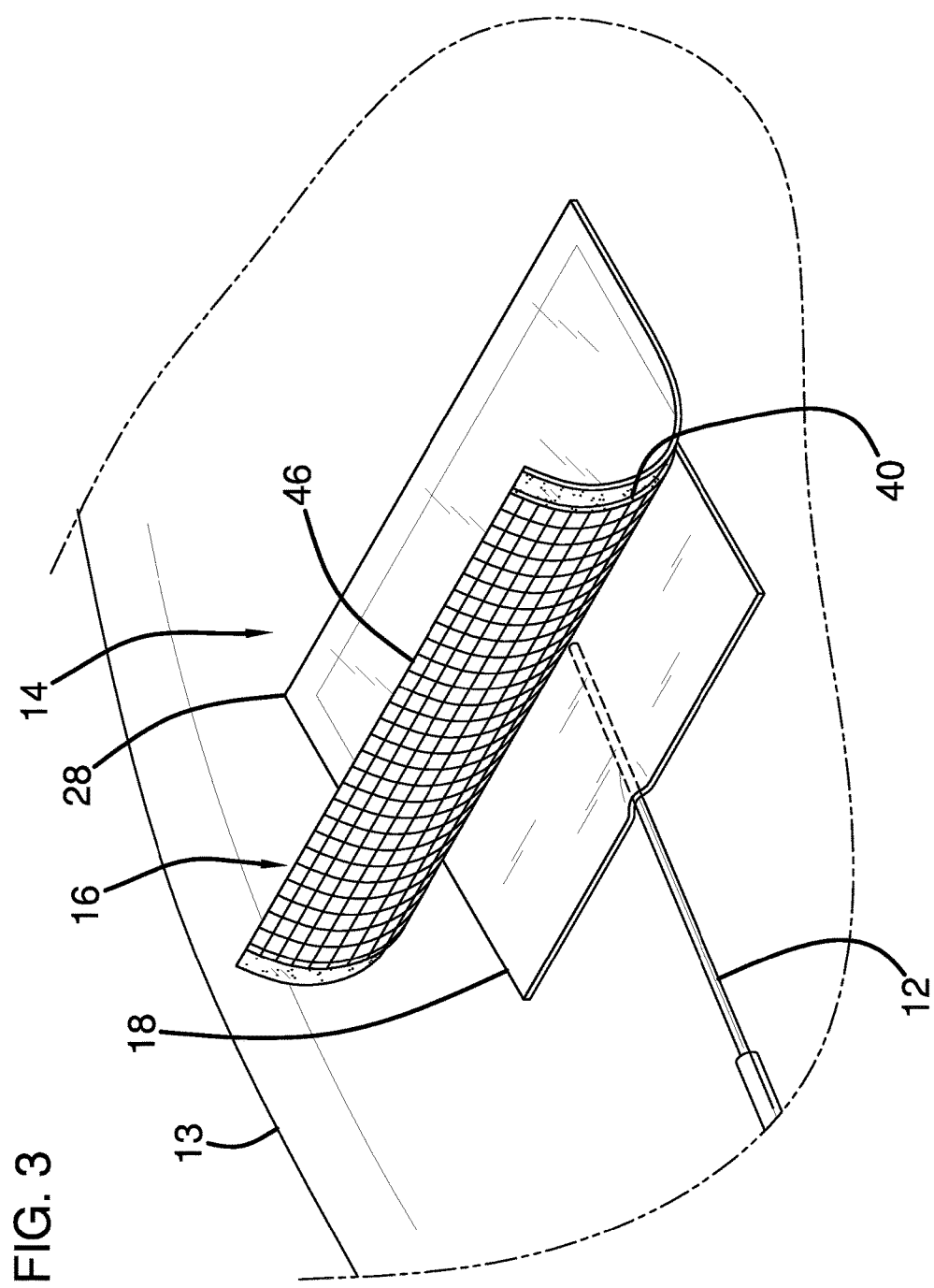
FIG. 3 is a perspective in-use view of an embodiment of the disclosure.

With reference now to the drawings, and in particular to FIGS. 1 through 4 thereof, a new dressing device embodying the principles and concepts of an embodiment of the disclosure and generally designated by the reference numeral 10 will be described.

As best illustrated in FIGS. 1 through 4, the catheter dressing system 10 generally comprises a catheter 12 that is selectively inserted into a patient 13 when the patient 13 is undergoing a surgical procedure. The catheter 12 may be a nerve block catheter, an intravenous needle or any other surgical catheter. A dressing 14 is provided and the dressing 14 may be adhered to the patient 13. The dressing 14 covers the catheter 12 thereby inhibiting the catheter 12 from being contaminated and the dressing 14 has a tear-away portion 16. The dressing 14 may be manufactured in a sterile environment thereby facilitating the dressing 14 to be employed in a sterile surgical environment.

The dressing 14 comprises a first panel 18 that has a first surface 20, a second surface 22 and a perimeter edge 24 extending therebetween. The first surface 20 abuts the catheter 12 when the dressing 14 is positioned on the patient 13. The first panel 18 is comprised of a fluid impermeable material to inhibit the catheter 12 from being contaminated. Moreover, the first panel 18 is comprised of a translucent material such that the catheter 12 is visible through the first panel 18.

A first adhesive layer 26 is coupled to the first surface 20 of the first panel 18 such the first adhesive layer 26 adhesively engages the catheter 12. The first adhesive layer 26 adhesively engages the patient 13 thereby retaining the first panel 18 on the patient 13. The first adhesive layer 26 may be comprised of a surgical grade adhesive or the like. The first panel 18 may have a length ranging between approximately 10.0 cm and 12.0 cm and a width ranging between approximately 7.0 cm and 10.0 cm.

The tear-away portion 16 comprises a second panel 28 that has a primary surface 30, a secondary surface 32 and a peripheral edge 34 extending therebetween. The peripheral edge 34 has a first side 36. A second adhesive layer 38 is coupled to the primary surface 30 and the second adhesive layer 38 may be comprised of a surgical grade adhesive or the like. The second panel 28 may have a length ranging between approximately 13.0 cm and 15.0 cm and a width ranging between approximately 10.0 cm and 12.0 cm.

The tear-away portion 16 further includes a third panel 40 that has an upper surface 42, a lower surface 43 and an exterior edge 44 extending therebetween. The exterior edge 44 has a first side 46. The upper surface 42 is adhered to the second adhesive layer 38. The exterior edge 44 is spaced inwardly from the peripheral edge 34 of the second panel 28 to define an exposed portion 48 of the second adhesive layer 38 extending between the exterior edge 44 and the peripheral edge 34. The first side 46 of the third panel 40 is oriented collinear with the first side 36 of the second panel 28. The lower surface 43 is removably attached to the second surface 22 of the first panel 18. The perimeter edge 24 of the first panel 18 is spaced inwardly from the exterior edge 44 of the third panel 40. The third panel 40 may be removably attached to the first panel 18 via a non residual adhesive or any other means of removable attachment.

A surgical drape 50 is provided and the surgical drape 50 may be positioned on the patient 13 when the patient 13 is undergoing the surgical procedure. The surgical drape 50 adhesively engages the tear-away portion 16 of the dressing 14. Moreover, the tear-away portion 16 is removed from the dressing 14 when the surgical drape 50 is removed from the patient 13. In this way the dressing 14 remains on the catheter 12 when the surgical drape 50 is removed.

In use, the catheter 12 is inserted into the patient 13 and the dressing 14 is applied over the catheter 12. The first adhesive layer 26 adhesively engages the catheter 12 and the patient 13 when the dressing 14 is applied over the catheter 12. Additionally, the exposed portion 48 of the second adhesive layer 38 adhesively engages the patient 13. The surgical drape 50 is positioned to cover the patient 13 and the surgical drape 50 adhesively engages the secondary surface 32 of the second panel 28. The surgical drape 50 is removed from the patient 13 when the surgical procedure is complete. Each of the second panel 28 and the third panel 40 are removed from the patient 13 when the surgical drape 50 is removed from the patient 13. The first panel 18 remains adhered to the catheter 12 and the patient 13 when the surgical drape 50 is removed. In this way the first panel 18 inhibits the catheter 12 from being removed when the surgical drape 50 is removed. Moreover, the first panel 18 continuously protects the catheter 12 from contamination when the surgical drape 50 is removed. The first panel 18 is removed from the patient 13 prior to removing the catheter 12 from the patient 13.

With respect to the above description then, it is to be realized that the optimum dimensional relationships for the parts of an embodiment enabled by the disclosure, to include variations in size, materials, shape, form, function and manner of operation, system and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A catheter dressing system facilitating a surgical drape to be removed from a catheter without exposing said catheter to contamination, said system comprising:
   a catheter being configured to be inserted into a patient when the patient is undergoing a surgical procedure;
   a dressing being configured to be adhered to the patient, said dressing covering said catheter thereby inhibiting said catheter from being contaminated, said dressing having a tear-away portion, said dressing comprising a first panel having a first surface, a second surface and a perimeter edge extending therebetween, said first surface abutting said catheter when said dressing is positioned on the patient, said tear-away portion of said dressing being removable from said first panel; and
   a surgical drape being configured to be positioned on the patient when the patient is undergoing the surgical procedure, said surgical drape adhesively engaging said tear-away portion of said dressing, said tear away portion being removed from said dressing when said surgical drape is removed from the patient such that said first panel of said dressing remains on said catheter.

2. The system according to claim 1, further comprising said first panel being comprised of a fluid impermeable material such that said first panel inhibits said catheter from being contaminated.

3. The system according to claim 2, further comprising a first adhesive layer being coupled to said first surface of said first panel such said first adhesive layer adhesively engages the catheter, said first adhesive layer being configured to adhesively engage the patient thereby retaining said first panel on the patient.

4. The system according to claim 1, wherein said tear-away portion comprises a second panel having a primary surface, a secondary surface and a peripheral edge extending therebetween, said peripheral edge having a first side.

5. The system according to claim 4, further comprising a second adhesive layer being coupled to said primary surface.

6. The system according to claim 5, further comprising a third panel having an upper surface, a lower surface and an exterior edge extending therebetween, said exterior edge having a first side, said upper surface being adhered to said second adhesive layer having said exterior edge being spaced inwardly from said peripheral edge of said second panel.

7. The system according to claim 6, wherein:
   said dressing includes a first panel having a second surface and a perimeter edge; and
   said lower surface being removably attached to said second surface of said first panel having said perimeter edge of said first panel being spaced inwardly from said exterior edge of said third panel.

8. A catheter dressing system facilitating a surgical drape to be removed from a catheter without exposing said catheter to contamination, said system comprising:
   a catheter being configured to be inserted into a patient when the patient is undergoing a surgical procedure;
   a dressing being configured to be adhered to the patient, said dressing covering said catheter thereby inhibiting said catheter from being contaminated, said dressing having a tear-away portion, said dressing comprising a first panel having a first surface, a second surface and a perimeter edge extending therebetween, said first surface abutting said catheter when said dressing is positioned on the patient, said first panel being comprised of a fluid impermeable material such that said first panel inhibits said catheter from being contaminated, and a first adhesive layer being coupled to said first surface of said first panel such said first adhesive layer adhesively engages the catheter, said first adhesive layer being configured to adhesively engage the patient thereby retaining said first panel on the patient;

said tear-away portion comprising:

a second panel having a primary surface, a secondary surface and a peripheral edge extending therebetween, said peripheral edge having a first side, a second adhesive layer being coupled to said primary surface, and a third panel having an upper surface, a lower surface and an exterior edge extending therebetween, said exterior edge having a first side, said upper surface being adhered to said second adhesive layer having said exterior edge being spaced inwardly from said peripheral edge of said second panel, said lower surface being removably attached to said second surface of said first panel having said perimeter edge of said first panel being spaced inwardly from said exterior edge of said third panel; and a surgical drape being configured to be positioned on the patient when the patient is undergoing the surgical procedure, said surgical drape adhesively engaging said tear-away portion of said dressing, said tear away portion being removed from said dressing when said surgical drape is removed from the patient such that said dressing remains on said catheter.

\* \* \* \* \*